(12) United States Patent
Lariviere

(10) Patent No.: US 9,586,702 B2
(45) Date of Patent: Mar. 7, 2017

(54) NITROUS OXIDE SYSTEM FOR PRODUCING BREATHING AIR

(75) Inventor: Brian W. Lariviere, Camarillo, CA (US)

(73) Assignee: Aerojet Rocketdyne of DE, Inc., Sacramento, CA (US)

( * ) Notice: Subject to any disclaimer, the term of this patent is extended or adjusted under 35 U.S.C. 154(b) by 1092 days.

(21) Appl. No.: 13/306,002

(22) Filed: Nov. 29, 2011

(65) Prior Publication Data

US 2013/0133662 A1 May 30, 2013

(51) Int. Cl.
| | |
|---|---|
| *A61M 16/10* | (2006.01) |
| *B64G 1/48* | (2006.01) |
| *C01B 13/02* | (2006.01) |
| *C01B 21/02* | (2006.01) |
| *B64G 1/22* | (2006.01) |

(52) U.S. Cl.
CPC ............ *B64G 1/48* (2013.01); *C01B 13/0203* (2013.01); *C01B 21/02* (2013.01); *A61M 16/10* (2013.01); *A61M 2202/0208* (2013.01); *A61M 2202/0266* (2013.01); *A61M 2202/0283* (2013.01); *B64G 2001/224* (2013.01)

(58) Field of Classification Search
CPC ........... A62B 7/08; A62B 9/003; A62B 13/00; A62B 21/00; A62B 23/04; A61M 16/18–16/186; A61M 16/105–16/107; A61M 16/104; A61M 16/0045; A61M 16/01; A61M 16/0078; A61M 16/0084; A61M 16/009; A61M 16/0093; A61M 2205/8237–2205/8256; A61M 2205/8212; A61M 2202/0078; A61M 2202/0283; A61M 16/10; B64G 1/48; C01B 13/0203; C01B 21/02
See application file for complete search history.

(56) References Cited

U.S. PATENT DOCUMENTS

| | | | | |
|---|---|---|---|---|
| 3,351,562 | A | * | 11/1967 | Taylor ............................ 514/771 |
| 3,729,002 | A | * | 4/1973 | Miller ....................... 128/205.26 |
| 3,876,773 | A | | 4/1975 | Bracken |
| 4,259,303 | A | * | 3/1981 | Nakaji et al. ............... 423/239.1 |
| 5,360,001 | A | * | 11/1994 | Brill et al. ................. 128/205.26 |
| 5,370,112 | A | * | 12/1994 | Perkins ..................... 128/204.21 |
| 7,165,546 | B2 | * | 1/2007 | Frankie et al. ........... 128/201.21 |
| 7,644,594 | B2 | * | 1/2010 | Berry et al. ..................... 62/617 |
| 2009/0031700 | A1 | | 2/2009 | Karabeyoglu |
| 2009/0148352 | A1 | | 6/2009 | Zubrin et al. |
| 2012/0000549 | A1 | * | 1/2012 | Thorne et al. ................. 137/455 |

\* cited by examiner

*Primary Examiner* — Valerie L Skorupa
(74) *Attorney, Agent, or Firm* — Carlson, Gaskey & Olds, P.C.

(57) ABSTRACT

A multi-function nitrous oxide system is disclosed for producing breathing air. The system includes a nitrous oxide storage container and a nitrous oxide conversion element connected with the nitrous oxide storage container. The nitrous oxide conversion element is downstream from the nitrous oxide storage container and produces hot fluid. The system includes a breathing air storage container connected with the nitrous oxide conversion element downstream from the nitrous oxide conversion element.

2 Claims, 1 Drawing Sheet

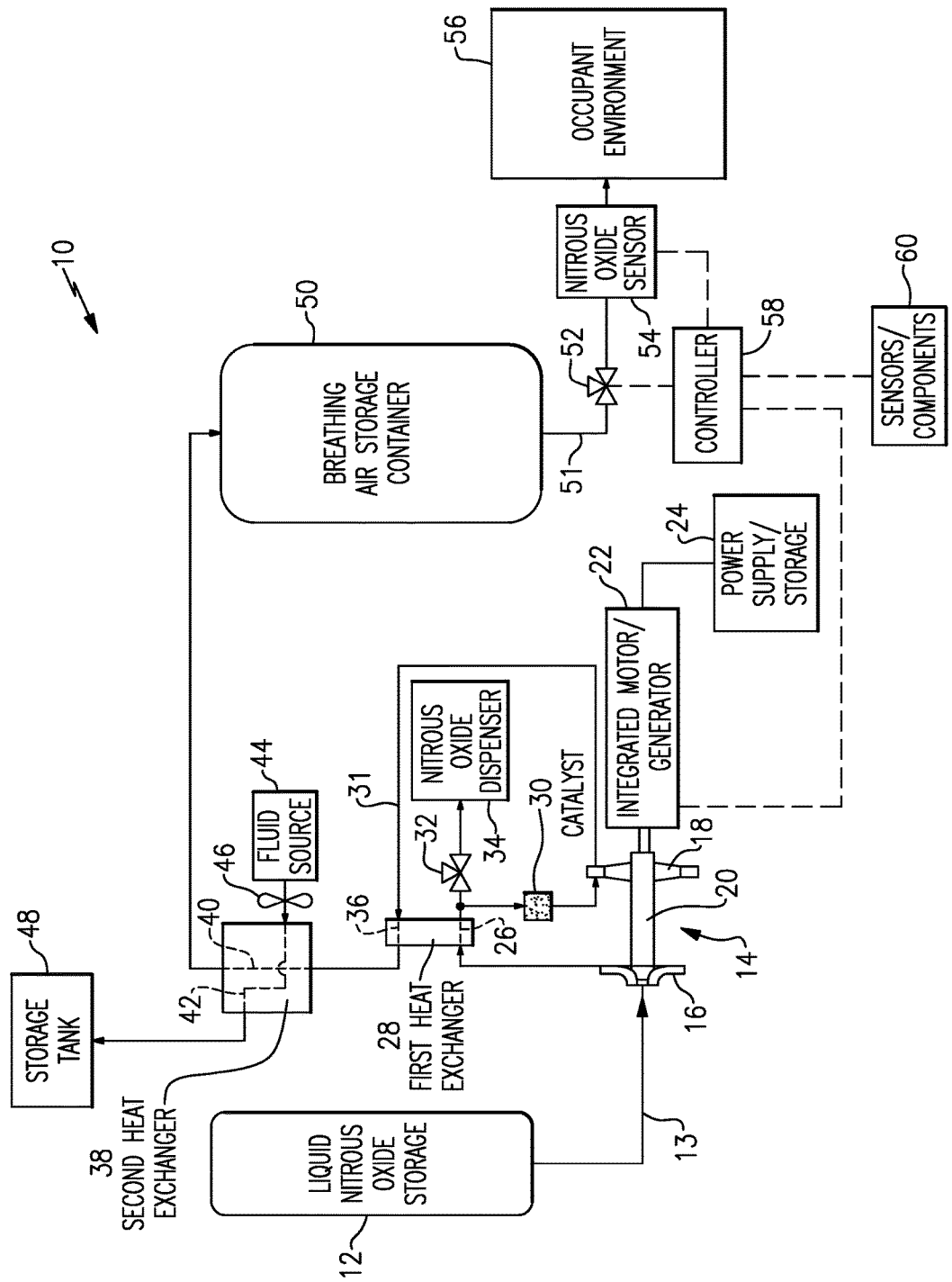

NITROUS OXIDE SYSTEM FOR PRODUCING BREATHING AIR

BACKGROUND

This disclosure relates to a multi-function nitrous oxide system for producing breathing air.

In environments in which breathing air is not readily available, it is desirable to produce the breathing air from sources, such as nitrous oxide. One type of breathing air production scheme produces a mixture of nitrogen and oxygen by decomposing nitrous oxide using a catalyst. In such schemes, the nitrous oxide is converted for the singular purpose of producing breathing air.

BRIEF DESCRIPTION OF THE DRAWINGS

The disclosure can be further understood by reference to the following detailed description when considered in connection with the accompanying drawings wherein:

The FIGURE schematically depicts an air supply system.

DETAILED DESCRIPTION

A synthetic air supply system 10 for producing breathing air is schematically illustrated in the FIGURE. The system 10 is suitable for use in space exploration missions, for example, in which an environment must be filled with breathing air prior to occupancy. The system 10 serves multiple purposes with its integrated functions.

The system 10 includes a liquid nitrous oxide storage container 12 filled with liquid nitrous oxide. A first fluid line 13 is fluidly connected to the liquid nitrous oxide storage container 12 and supplies the liquid nitrous oxide to a charging system 14. In the example, the charging system 14 includes a pump 16 and a turbine 18 mounted on a shaft 20. An integrated motor/generator 22 is coupled to the shaft 20. A power supply/storage 24 is in communication with the motor/generator 22.

The pump 16 is arranged in the first fluid line 13 to convey the nitrous oxide through the system 10. A first heat exchanger 28 includes first and second passages 26, 36. The first fluid line 13 provides the first passage 26. A nitrous oxide conversion element, such as a catalyst 30, is fluidly connected to the first fluid line 13 downstream from the first heat exchanger 28. Thus, the pump 16 is in fluid communication with the liquid nitrous oxide storage container 12 and the catalyst 30, and the turbine 18 is in fluid communication with an output of the catalyst 30. The catalyst 30 is configured to decompose the nitrous oxide into nitrogen and oxygen gas. A second fluid line 31, which provides the second passage 36, is in fluid communication with the catalyst 30 to convey nitrogen and oxygen. The first and second passages 26, 36 are configured to transfer heat from the second passage 36 to the first passage 26.

In one example, a nitrous oxide supply is in fluid communication with the first fluid line 13. The nitrous oxide supply is arranged upstream from the catalyst 30 in the example shown. In the example, the nitrous oxide supply includes a valve 32 that selectively provides nitrous oxide to a nitrous oxide dispenser 34, such as a mask for medical use. In this manner, nitrous oxide, which is an anesthetic, can be provided to a user in the event of a serious injury.

A second heat exchanger 38 is arranged downstream from the first heat exchanger 28. The second fluid line 31 includes a third passage 40 arranged in the second heat exchanger 38. A fourth passage 42, which provides a fluid supply to be heated, is also arranged within the second heat exchanger 38 to receive rejected heat from the second fluid line 31. In the example, the fluid from a fluid source 44, such as a water reservoir, ambient gases or other process fluids, passes through the second heat exchanger to a destination 48, such as a storage tank or outside environment. A blower 46 may be used to convey the fluid through the fourth passage 42.

A breathing air storage container 50 is in fluid communication with and arranged downstream from the second fluid line 31. The breathing air storage container 50 stores a mixture of two-thirds nitrogen gas and one-third oxygen gas. A third fluid line 51 is in fluid communication with and arranged downstream from the breathing air storage container 50. A control valve 52 is arranged in the third fluid line 51 and regulates the breathing air to an occupant environment 56, which stores an output from the turbine 18. A nitrous oxide sensor 54 may be arranged in the third fluid line 51 to detect unwanted nitrous oxide that might enter the occupant environment 56.

A controller 58 is schematically illustrated in the FIGURE. The controller 58 provides commands and communicates with, for example, the motor/generator 22, the control valve 52, nitrous oxide sensor 54, and other sensors and/or components 60 used in the system. In one example, the occupant environment 56 provides living environment that is an inflatable habitat. The habitat may be movable from an uninflated condition to an inflated condition in response to a command from the controller 58, which would inflate the habitat with nitrogen and oxygen produced by the system 10.

In operation, the system 10 is started by driving the pump 16 with the motor/generator 22, which is powered by the power supply 24. The pump 16 conveys the nitrous oxide to the catalyst 30, which decomposes the nitrous oxide into nitrogen and oxygen, which may be at temperatures exceeding 1000° F. (540° C.). This heated gas passes through the turbine 18, which then will drive the pump 16 such that external power from the power supply 24 is no longer necessary. The motor/generator 22, now driven by the turbine 18, may be used to charge the power supply/storage 24. An alternative method for starting the system without the use of the power supply/storage 24 would be to initiate flow to the catalyst 30 and allow the heated gas power the turbine 18 and slowly increase the power to the shaft 20 and increases the flow through the pump 16 until it reaches the desired production capacity.

The heated gases within the second passage 36 rejects heat to the first passage 26, heating the nitrous oxide entering the catalyst 30 thereby improving its efficiency. The heated gases flowing through the third passage 40 reject heat to the fluid flowing through the fourth passage 42, lowering the temperature of the nitrogen and oxygen to a level more readily useable by an occupant of the occupant environment 56.

Although an example embodiment has been disclosed, a worker of ordinary skill in this art would recognize that certain modifications would come within the scope of the claims. For that reason, the following claims should be studied to determine their true scope and content.

What is claimed is:

1. A nitrous oxide system for producing breathing air, the nitrous oxide system comprising:
   a nitrous oxide storage container configured to store nitrous oxide;
   a nitrous oxide conversion element fluidly connected with the nitrous oxide storage container by a first fluid line, the nitrous oxide conversion element arranged downstream from the nitrous oxide storage container and configured to produce hot fluid;

a breathing air storage container fluidly connected with the nitrous oxide conversion element by a second fluid line, the breathing air storage container arranged downstream from the nitrous oxide conversion element;

a charging system in communication with the second line and configured to charge a power supply in response to the hot fluid;

a first heat exchanger through which the first and second fluid lines pass, the nitrous oxide conversion element arranged fluidly between the first and second fluid lines; and a second heat exchanger fluidly arranged downstream from the first heat exchanger, the second fluid line passing through the second heat exchanger, and a passage passing through the second heat exchanger configured to receive heat rejected from the second fluid line.

2. A nitrous oxide system for producing breathing air, the nitrous oxide system comprising:

a nitrous oxide storage container configured to store nitrous oxide;

a nitrous oxide conversion element fluidly connected with the nitrous oxide storage container by a first fluid line, the nitrous oxide conversion element arranged downstream from the nitrous oxide storage container and configured to produce hot fluid;

a breathing air storage container fluidly connected with the nitrous oxide conversion element by a second fluid line, the breathing air storage container arranged downstream from the nitrous oxide conversion element; and a heat exchanger having the second fluid line passing therethrough, and a passage passing through the heat exchanger and configured to receive heat rejected from the second fluid line and provide the rejected heat to a destination;

wherein the heat exchanger is a second heat exchanger, and comprising a first heat exchanger through which the first and second fluid lines pass, the nitrous oxide conversion element arranged fluidly between the first and second fluid lines, and the second heat exchanger fluidly arranged downstream from the first heat exchanger.

* * * * *